United States Patent
Distler et al.

(10) Patent No.: US 7,170,975 B2
(45) Date of Patent: Jan. 30, 2007

(54) METHOD FOR OPERATING A COMPUTED TOMOGRAPHY APPARATUS HAVING A DIAPHRAGM AT THE RADIATION DETECTOR

(75) Inventors: Friedrich Distler, Fürth (DE); Matthias Seufert, Pettstadt (DE); Christoph Süss, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 77 days.

(21) Appl. No.: 10/527,875

(22) PCT Filed: Sep. 1, 2003

(86) PCT No.: PCT/DE03/02890

§ 371 (c)(1),
(2), (4) Date: Mar. 16, 2005

(87) PCT Pub. No.: WO2004/026141

PCT Pub. Date: Apr. 1, 2004

(65) Prior Publication Data

US 2006/0050841 A1    Mar. 9, 2006

(30) Foreign Application Priority Data

Sep. 16, 2002  (DE) ................ 102 42 920

(51) Int. Cl.
*G21K 1/04*      (2006.01)

(52) U.S. Cl. ............... 378/150; 378/15; 378/147
(58) Field of Classification Search .......... 378/15, 378/147–152; 250/505.1

See application file for complete search history.

(56) References Cited

U.S. PATENT DOCUMENTS

| 4,691,335 A | 9/1987 | Telorack .................. 378/152 |
| 5,299,250 A | 3/1994 | Styrnol et al. ............. 378/19 |
| 5,406,611 A | 4/1995 | Schobert et al. ........... 378/152 |
| 5,644,614 A | 7/1997 | Toth et al. ................. 378/147 |
| 6,396,902 B2 | 5/2002 | Tybinkowski et al. ...... 378/150 |
| 6,449,340 B1 | 9/2002 | Tybinkowski et al. ...... 378/150 |
| 6,501,828 B1 * | 12/2002 | Popescu .................. 378/150 |
| 2003/0086534 A1 | 5/2003 | Seufert .................... 378/150 |
| 2003/0112924 A1 | 6/2003 | Seufert .................... 378/160 |

FOREIGN PATENT DOCUMENTS

| DE | OS 38 18 542 | 12/1989 |
| DE | OS 101 45 997 | 4/2003 |

* cited by examiner

*Primary Examiner*—Edward J. Glick
*Assistant Examiner*—Jurie Yun
(74) *Attorney, Agent, or Firm*—Schiff Hardin LLP

(57) ABSTRACT

In a method for operating a computed tomography apparatus, having an x-ray source rotatable around a system axis and a radiation detector with a detector-proximate beam-gating diaphragm, and a patient support, a spiral scan of a patient on the patient support is conducted by rotating the x-ray source around the system axis while moving the subject on the patient support substantially parallel to the system axis. The diaphragm have movable absorber elements that are curved, and are moved independently of each other toward and away from each other in a direction substantially parallel to the system axis during the spiral scan. The absorber elements are dynamically adjusted in an asymmetrical manner during the spiral scan to reduce overexposure of the examination subject to x-rays.

12 Claims, 6 Drawing Sheets

METHOD FOR OPERATING A COMPUTED TOMOGRAPHY APPARATUS HAVING A DIAPHRAGM AT THE RADIATION DETECTOR

This application is a continuation of PCT/DE 03/02890, Sep. 1, 2003.

BACKGROUND OF THE INVENTION

1. Field of the Invention

The present invention concerns a method for operating a computed tomography apparatus with an x-ray radiator rotatable around a system axis, with an x-ray detector and with a radiator-side gating device that has two opposite absorber elements that can be adjusted in a straight line, in particular that can be adjusted with regard to their separation from one another, for variable delimitation of the ray beam. An examination subject is scanned during rotation of the x-ray radiator and relative translational movement between the x-ray radiator and the examination subject in the direction of the system axis.

2. Description of the Prior Art

In an examination of an examination subject or a patient in an x-ray diagnostic apparatus, the examination subject is moved into an x-ray beam emitted by an x-ray source, and the radiation actuated by the subject is detected by an x-ray detector. The examination subject is thus located in the beam path between the x-ray source and the x-ray detector. The typical x-ray tubes used as x-ray radiators emit x-ray radiation in a significantly larger solid angle than is necessary for examination at the patient. In order to prevent unnecessary radiation exposure at the patient, unnecessary x-rays are gated (blanked out). For this, in conventional x-ray apparatuses it is known to dispose a radiator-side gating device immediately after the x-ray radiator in the beam path. Such gating device is also designated as a primary beam diaphragm. For example, such a primary beam diaphragm, with diaphragm plates that can be moved opposite to one another as absorber elements, is known from European Application 0 187 245.

In computed tomography apparatuses with multi-row x-ray detectors, a detector-side beam diaphragm (or a beam diaphragm near to the detector) that is mounted in the beam path between the patient and the x-ray detector is also frequently used in addition to a radiator-side gating device that is arranged in the beam path between the x-ray radiator and the patient. It is thereby possible to shadow one or more detector rows of the multiple detector rows and to use the remaining detector rows as active detector rows.

Such a collimator is known from U.S. Pat. No. 6,396,902 the entire bearing body composed of x-ray-absorbing material must be moved. This occurs by rotation of the bearing body, which is why the bearing body is also curved around a second axis. In order to also be able to bring another diaphragm slit into the matching position, the rotation axis would have to be located at the height of the focus of the x-ray radiator. This is at best possible with very large mechanical effort.

Alternatively, the rotated bearing body would have to be readjusted into the correct position via a shifting movement, which is likewise very elaborate. Moreover, the production of a bearing body curved around two axes is expensive, because this must also be produced from x-ray-absorbing material, meaning from a material with a high atomic number.

A further disadvantage of the x-ray collimator known from U.S. Pat. No. 6,396,902 is that only a finite number of slits of discrete width can be applied or, respectively, introduced on or in the bearing body.

SUMMARY OF THE INVENTION

An object of the present invention is to provide a method for operating a computed tomography apparatus having a beam-gating diaphragm disposed near and preceding the radiation detector, wherein over-radiation of the patient at the beginning and at the end of a scan are avoided.

The above object is achieved in accordance with the present invention in a method for operating a computed tomography apparatus wherein the movable elements of a beam-gating diaphragm disposed preceding the radiation detector are adjusted in an asymmetrical manner.

According to the invention, this object is achieved by a method for operation of a computed tomography apparatus with a radiator-side gating device having absorber elements exhibiting a curved shape. The gating device has an adjustment device that acts on the absorber elements such that the absorber elements can be moved perpendicularly to their longitudinal direction, so they can be adjusted (displaced) relative to one another. The elements can be moved in a direction parallel to the system axis. The absorber elements exhibit the curved shape at their outer contour that delimits the x-ray beam, i.e. for example at an edge forming a diaphragm slit.

To prevent unnecessary radiation exposure for the examination subject, the gating device is operated in accordance with the inventive method with absorber elements opened to different widths with regard to a center beam of the active, (i.e. radiation detecting) surface of the x-ray detector. This prevents over-radiation of the patient at the beginning and at the end of a scan movement of a scan (in particular a spiral scan), by allowing the gating device to be adjusted quasi-asymmetrically.

For example, before the beginning and/or after the end of the scan movement, in particular the relative movement, one of the absorber elements is positioned in a closed position and the other absorber element is positioned in an open position.

After the beginning of the scan movement, in particular the relative movement, the absorber element located in the closed position is preferably opened in synch with the scan movement, in particular with the relative movement.

It is likewise possible that, before the end of the scan movement (in particular the relative movement), one of the absorber elements located in the open position is closed in synchronization with the scan movement, in particular with the relative movement.

A dynamic variation of the collimation width is thus effected with the gating device.

In an advantageous manner, the slit width is continuously or freely selectable between the curved absorber elements or diaphragm jaws, and thus the slice thickness that is adjustable at the computed tomography apparatus can assume non-discrete values. Wide detector rows can be only partially irradiated, and thus slices that are thinner than the width of the detector elements are also possible in a simple manner.

Moreover, the gating device requires absorber elements that are necessarily curved only in one direction or in one plane and thus exhibit, for example, a shape as is created given bending of a plate around a straight edge (for example "banana shape"). The gating device can thus also be produced simply.

The variation that is continuous to the greatest possible extent, of the slit width or the collimation width possible in the computed tomography apparatus allows—as already mentioned—a free selection of the slice thickness and a flexible selection of the active rows of detector elements. However, a readjustment of the diaphragm setting given a change of the focus size in the x-ray receiver occurring during the operation is still possible.

Since the absorber elements can be moved independently of one another, it is possible to move the absorber elements not only opposite one another, but also concurrently in the same direction. For example, a diaphragm readjustment is possible given a variation of the focus position in the diaphragm rays that occurs during the operation (focal spot tracking). This means that the entire slice can also be shifted in the z-direction with a constant slice width. Moreover, a dynamic variation of the collimation width is possible, whereby (for example) an unwanted over-radiation at the beginning and at the end of a spiral scan can be reduced, by one of the absorber elements remaining closed at the beginning of the scan and only being opened at the beginning of the scan with the beginning of the translational patient bed movement in the direction of the system axis. The same is true in reverse for the end of the scan.

The adjustment device for each of the absorber elements indicates a separate adjustment unit, whereby the adjustment units are preferably fashioned for linear movement of the appertaining absorber element. With such a linear movement, it is ensured in an advantageous manner that sections of the curved absorber element matching one another still lie opposite one another after a relative movement in the direction of the system axis.

Each adjustment unit has a (preferably mutual) linear guide as well as a drive acting on the absorber elements.

As an alternative, each adjustment unit can have a linear motor, for example with a corresponding guide.

The curvature of the absorber elements proceeds in a plane perpendicular to the system axis. The curvature in particular exhibits the shape of a circular arc whose center point lies in the focus of the x-ray radiator. Identical distances between the focus and all ray-delimiting edge regions of the absorber elements are thereby achieved in a simple manner.

According to another embodiment, the curvature radii of the absorber elements differ from one another by a value of 0.5% to 10% from the interval. The advantage that results from this is to enable a hundred-percent closure of the diaphragm, because due to finishing tolerances it is normally not sufficient for the absorber elements to cease movement upon coming into contact with stop. Rather, they must at least slightly overlap, viewed in the direction of the x-ray beam. Such an overlapping is possible in an advantageous manner without scraping as a result different curvature radii.

DESCRIPTION OF THE PREFERRED EMBODIMENTS

Figure 1:
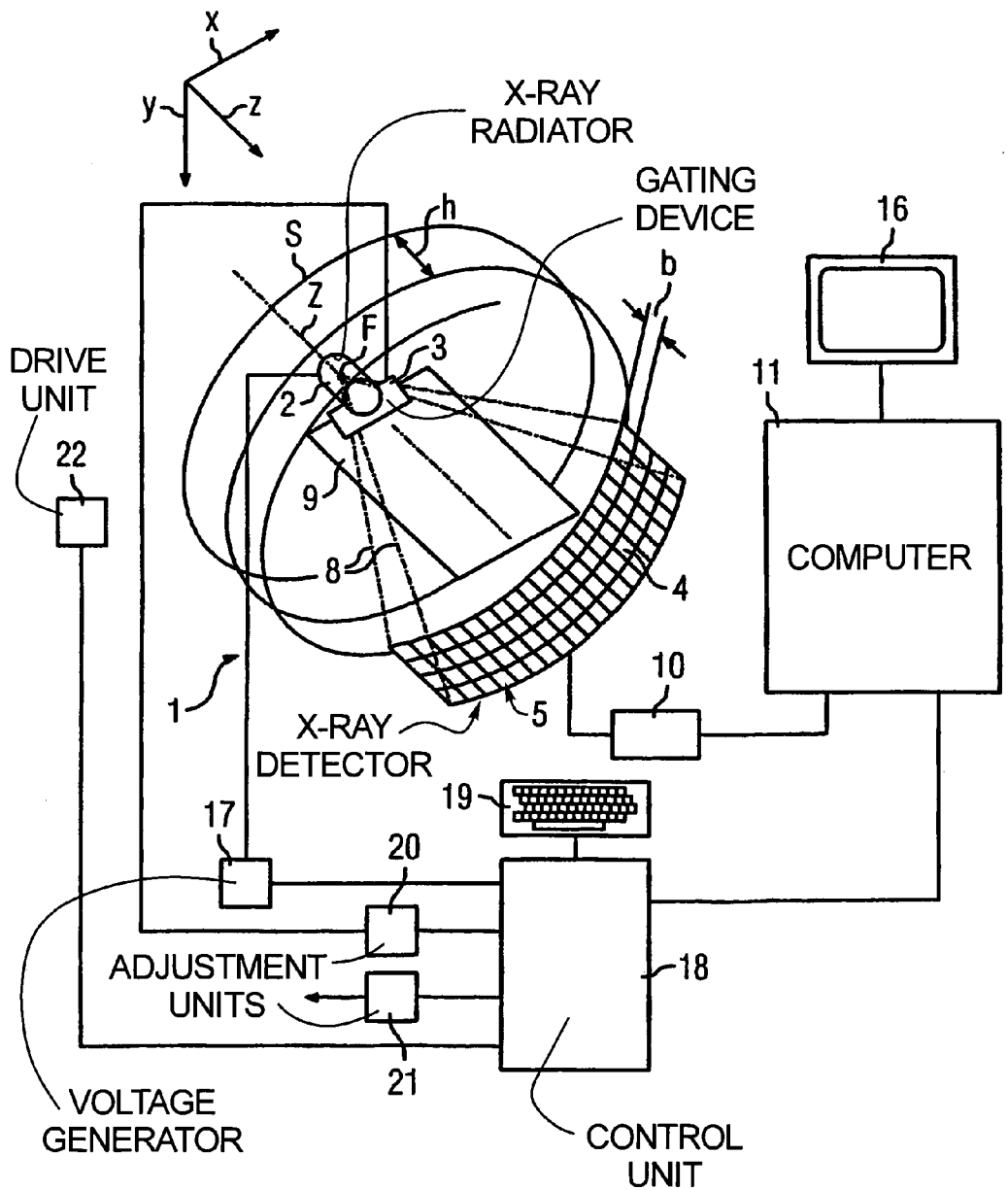
FIG. 1 schematically illustrates the basic components of a computed tomography apparatus operable in accordance with the inventive method.

A CT apparatus of the third generation is shown in FIG. 1 in section. Its data acquisition arrangement includes an x-ray radiator 2 with a gating device 3 positioned in front of it, near the source, and an x-ray detector 5, fashioned as a laminar array of a number of rows and columns of detector elements (one of these is designated 4 in FIG. 1), with an optional beam diaphragm (not shown) positioned in front of the x-ray detector 5, close to the detector 5. For clarity, in FIG. 1 only four rows of detector elements 4 are shown; however, the x-ray detector 5 can have further rows of detector elements 4, optionally also with different widths b.

The x-ray radiator 2 with the gating device 3 on one side and the x-ray detector 5 with its beam diaphragm on the other side are mounted opposite one another on a rotary frame (gantry) (not shown), such that a pyramidal x-ray beam emitted by the x-ray radiator 2 in the operation of the CT apparatus 1 and gated by the adjustable gating device 3 (the ray beams of which x-ray beam are designated with 8) strikes the x-ray detector 5. By means of the gating device 3 and, if applicable, by means of the detector-proximate beam diaphragm, a cross-section of the x-ray beam is adjusted such that only that region of the x-ray detector 5 is uncovered (exposed) that can be directly struck by the x-ray beam. In the operating mode illustrated in FIG. 1, there are four rows of detector elements that are designated as active rows. If applicable, further existing rows are covered by the detector-proximate beam diaphragm and are therefore not active. The gating device 3 primarily serves to prevent an unnecessary radiation exposure of the examination subject, in particular a patient, by keeping rays that otherwise do not arrive at the active rows away from the examination subject or patient.

The rotary frame can be rotated around a system axis Z by means of a drive unit. The system axis Z is parallel to the z-axis of a spatial rectangular coordinate system shown in FIG. 1.

The columns of the x-ray detector 5 likewise proceed in the direction of the z-axis, while the rows (whose width b is measured in the direction of the z-axis and is, for example, 1 mm) proceed to the system axis Z and the z-axis.

In order to be able to bring the examination subject, for example the patient, into the beam path of the x-ray beam, a support device 9 is provided that can be shifted parallel to the system axis Z, thus in the direction of the z-axis, such that a synchronization exists between the rotational movement of the rotary frame and the translational movement of the support device 9 with the ratio of translation speed to rotation speed constant. This ratio is adjustable by setting a desired value selected for the infeed h of the support device 9 per rotation of the rotary frame.

A volume of an examination subject located on the support device 9 can thus be examined in the course of a volume scanning. The volume scanning is effected in the form of a spiral scan in the sense that, during rotation of the rotary frame and simultaneous translation of the support device 9 per rotation of the rotary frame, a number of projections are acquired from various projection directions. During the spiral scan, the focus F of the x-ray radiator 2 moves on a spiral track S relative to the support device 9. A sequence scan is also possible as an alternative to this spiral scan.

The measurement data, read out in parallel during the spiral scan from the detector elements 4 of each active row of the detector system 5 and corresponding to the individual projections, are subjected to a digital-analog conversion in a data processing unit 10, and are serialized and transferred to an image computer 11 which shows the result of an image reconstruction on a display unit 16, for example a video monitor.

The x-ray radiator 2, for example an x-ray tube, is supplied with the necessary voltages and currents by a generator unit 17 (optionally likewise mutually rotating). In order to be able to adjust this to the respectively necessary values, a control unit 18 with keyboard 19 that allows the necessary adjustments is associated with the generator unit 17.

All operation and control of the CT apparatus 1 ensues by means of the control unit 18 and the keyboard 19, with the control unit 18 is connected with the image computer 11.

Among other things, the number of the active rows of detector elements 4 (and therewith the position the gating device 3 and of the optional detector-proximate beam diaphragm) can be adjusted, for which purpose the control unit 18 is connected with adjustment units 20 and 21 associated with the gating device 3 and the optional detector-proximate beam diaphragm. Furthermore the rotation time that the rotary frame requires for a complete rotation can be adjusted by means of the drive unit 22 associated with the rotary frame being connected with the control unit 18.

Figure 2:
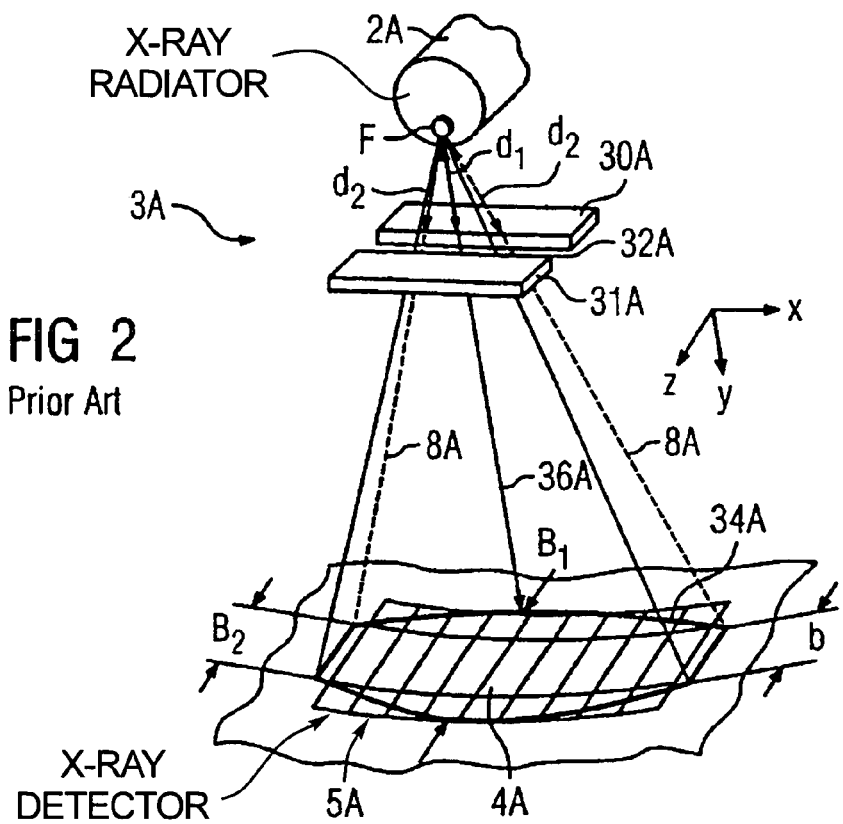
FIG. 2 schematically illustrates the structure and operation of a conventional radiation detector-proximate beam-gating diaphragm.

FIG. 2 shows the gating that results with a known gating device 3A with two separate absorber elements 30A, 31A. Shown is an x-ray beam with edge rays 8A that emanates from a focus F of an x-ray radiator 2A.

Both edge rays 8A emanating from the focus F and passing the (in FIG. 2) rear absorber element 30A respectively cover a distance d2 from the absorber element 30A. In contrast to this, the comparable distance d1 in the indicated central ray 36 is less than in the edge rays 8A. This is also true for the edge rays on the opposite side of the slit 32A. The result is that an x-ray beam whose outer contour 34A is not rectangular is gated on the x-ray detector 5A with its individual detector elements 4A shown in cross-section. In order to fully irradiate all detector elements 4A of the detector row (with width b, the outer contour 34A must be set such that its width B2 at the edge approximately corresponds to the width b of the detector row. As a result of the different distances $d_1 \neq d_2$, a larger width B1 of the outer contour 34A of the x-ray beam then results in the middle of the detector row. The portion of the x-ray beam occurring in this barrel-shaped region (here shown exaggerated, but nevertheless disturbing with regard to the radiation dose) is ultimately not used.

Figure 3:
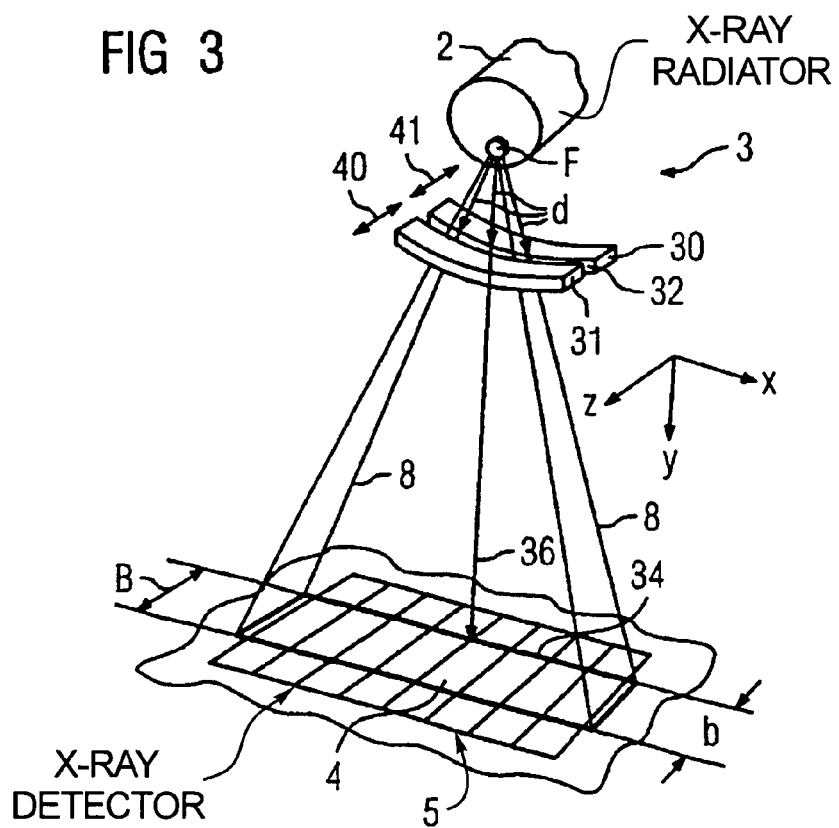
FIG. 3 schematically illustrates the radiation detector-proximate beam-gating diaphragm of the CT apparatus of FIG. 1, operable in accordance with the inventive method, in a perspective view.

The gating device 3 of the CT apparatus 1 according to the invention according to FIG. 1 is illustrated in FIG. 3 in a schematic representation and perspective view. The gating device 3 has two curved absorber elements 30, 31, between which a slit 32 is formed that can pass the x-rays emanating from the focus F of the x-ray radiator 2. The absorber elements 30, 31 (produced from heavy metal, for example tungsten and/or tantalum) are curved in a circular arc, with the middle point of the circular arc lying in the focus F of the x-ray radiator 2. It is thereby ensured that the respective spacings of the edge rays 8 and of a central ray 36 respectively measured from the focus F to the absorber elements 30 (or 31), exhibit the same value d. In an advantageous manner, this causes the x-ray beam gated by the x-ray detector 5 to exhibit in cross-section a rectangular outer contour 34 whose constant width B can be precisely adapted to the width b of one or more detector rows.

Both absorber elements 30, 31 can be moved or driven independently of one another, in parallel or opposite, which is indicated by corresponding double arrows 40, 41 in FIG. 3.

Figure 4:
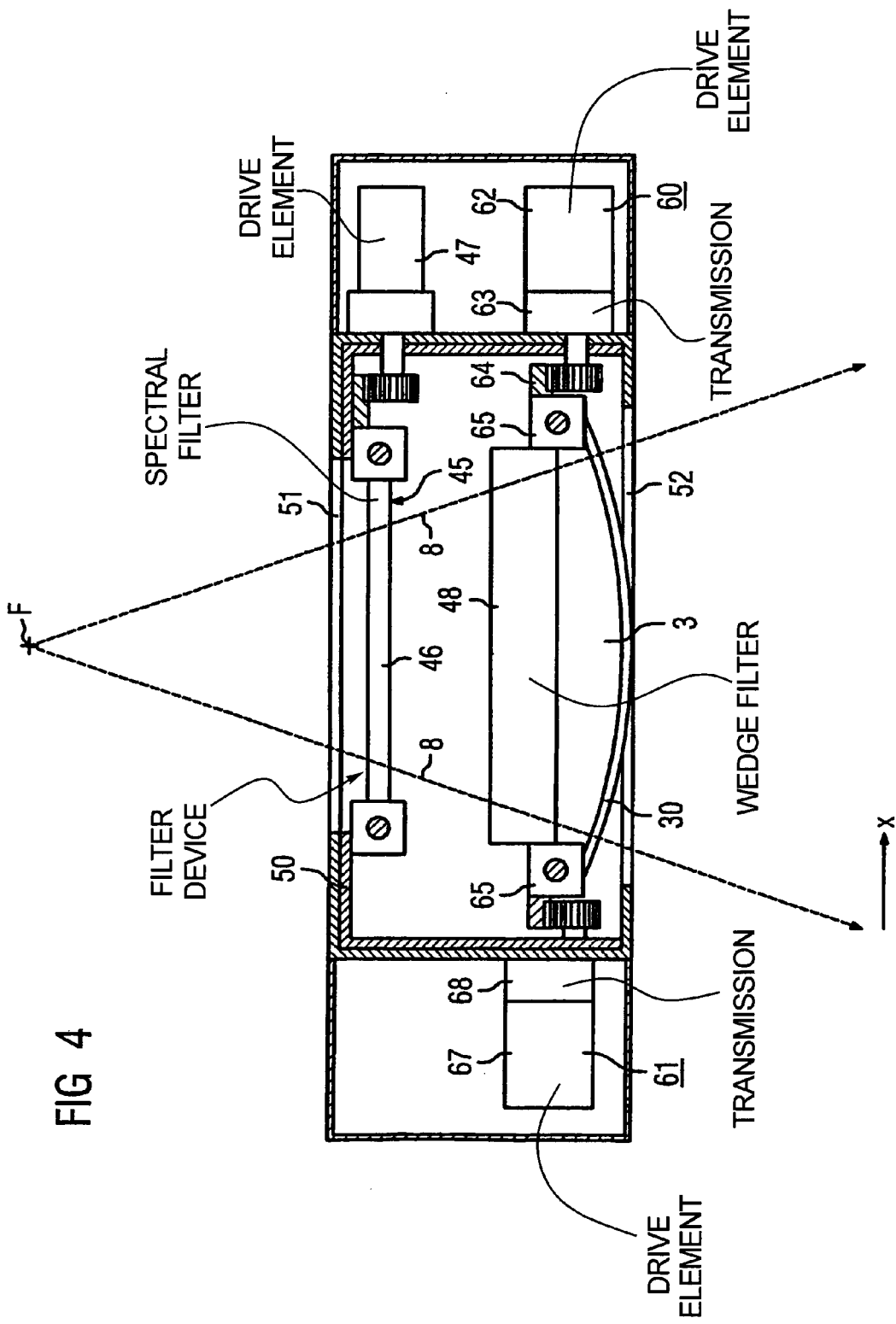
FIG. 4 is a sectional view through a first embodiment of the diaphragm of FIG. 3, operable in accordance with the inventive method.

FIG. 4 shows how the gating device 3 (shown schematically) can be accommodated in a common housing 50, together with a filter device 45 with one or more (copper) spectral filters 46 (with drive element 47 belonging to the filter changer) and with a wedge filter 48 serving for variable attenuation of the x-ray beam. The housing 50 has an entrance opening 51 on the side of the focus F and an exit opening 52 on the opposite side.

Moreover, FIG. 4 shows a separate adjustment unit 60 and 61 for each of the absorber elements 30, 31, with which the absorber elements 30, 31 can be moved linearly, independently of one another. In the exemplary embodiment of FIG. 4, the first adjustment unit 60 for one of the absorber elements 30 includes a first drive 62 fashioned as a step motor, which acts on one of the absorber elements 30 via a first transmission 63 and via a first toothed belt 64. For the other absorber element 31 (not visible in FIG. 4), a second drive 67 (likewise fashioned as a step motor) and a second transmission 68 are correspondingly present in the second adjustment unit 61. Both drive units 62, 67 act (for example via different spindle guides) on the two absorber elements 30, 31 moving linearly in the z-direction on the same linear guide 65.

Figure 5:
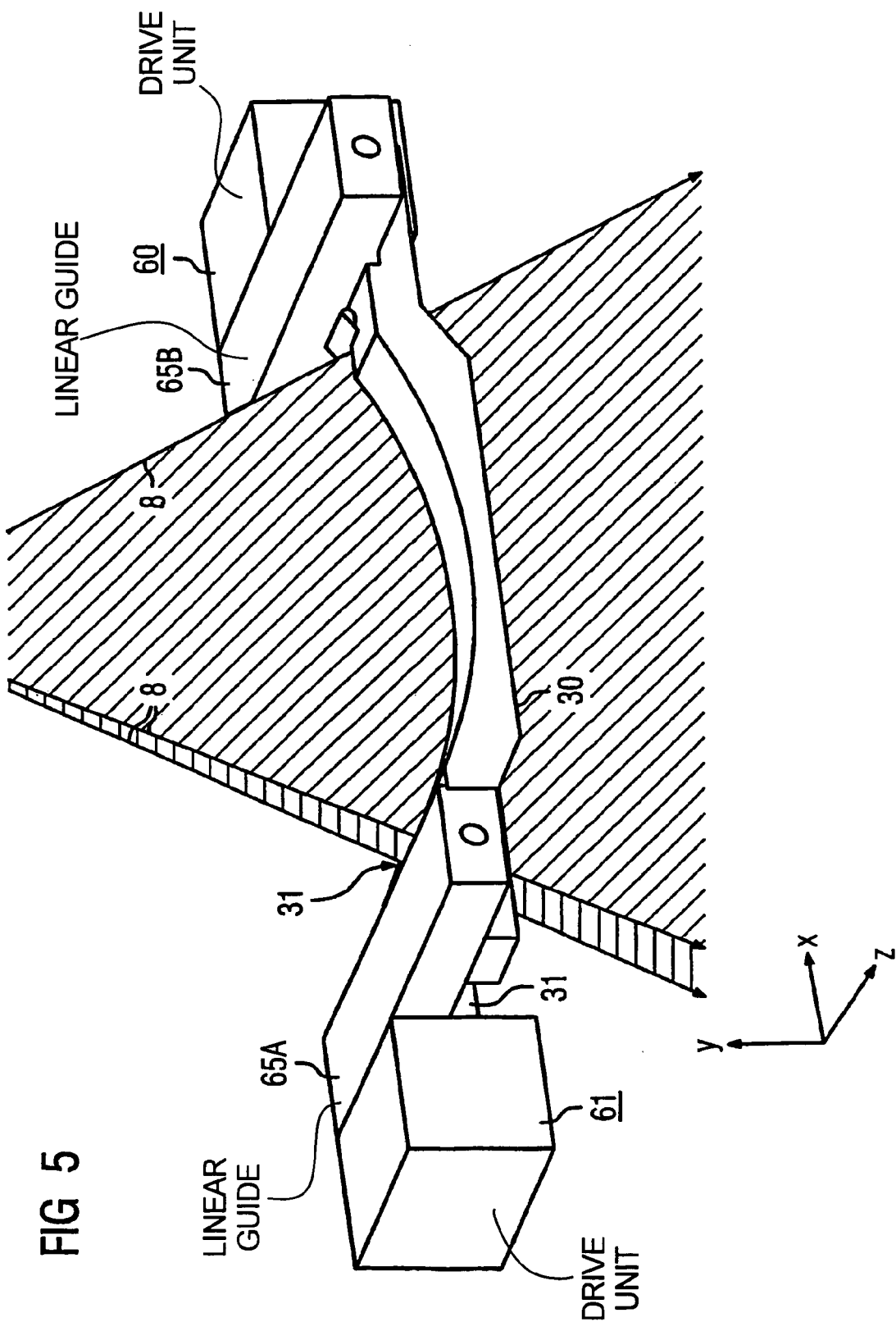
FIG. 5 is a perspective view of a second embodiment of the diaphragm of FIG. 3, operable in accordance with the inventive method.

The gating device 3 according to FIG. 3 is shown in FIG. 5 in a perspective representation according to a second exemplary embodiment. The special banana-like shape of the diaphragm backs 30, 31 is better visible in FIG. 5. Moreover, it can be seen in FIG. 5 that the common linear guide 65 can have a left-side first track 65A as well as a right-side second track 65B.

Figure 6:
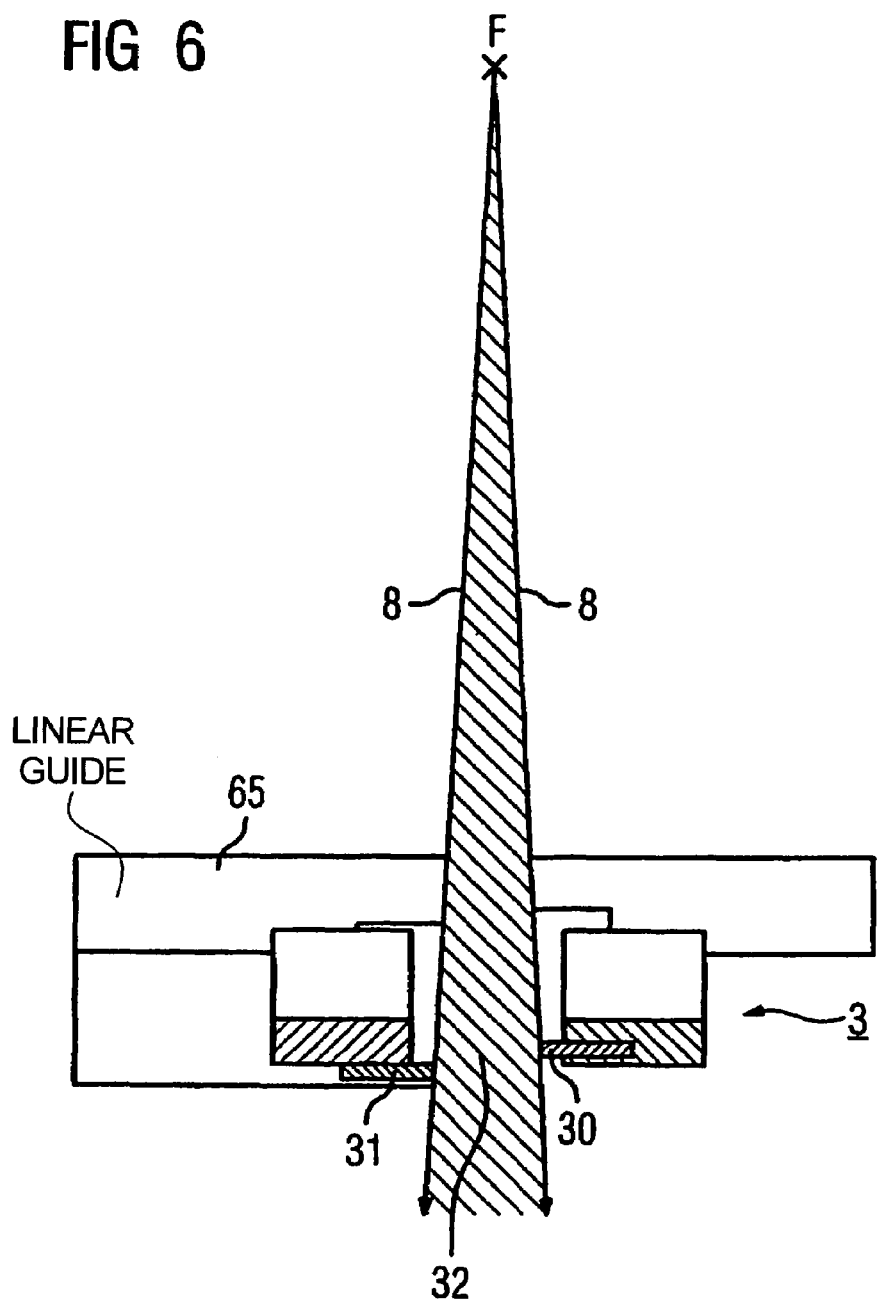
FIG. 6 is a sectional view of the second embodiment of the diaphragm shown in FIG. 5, operable in accordance with the inventive method.

The gating device 3 of FIG. 5 is explained again in FIG. 6 in a cross-section representation in the z-direction. In FIG. 6 it can be seen that the absorber elements 30, 31 are slightly displaced relative to one another in the height direction y, essentially corresponding to the direction of the radiated x-ray beam, in order to prevent passage of x-ray radiation (dependent on finishing tolerances) given a complete closing of the gating device 3.

In order to be able to execute the overlap of the absorber elements 30, 31 without friction, it is advantageous that the curvature radii of the absorber elements are slightly different. For example, these are 197 mm and 200 mm, respectively.

Figure 7:
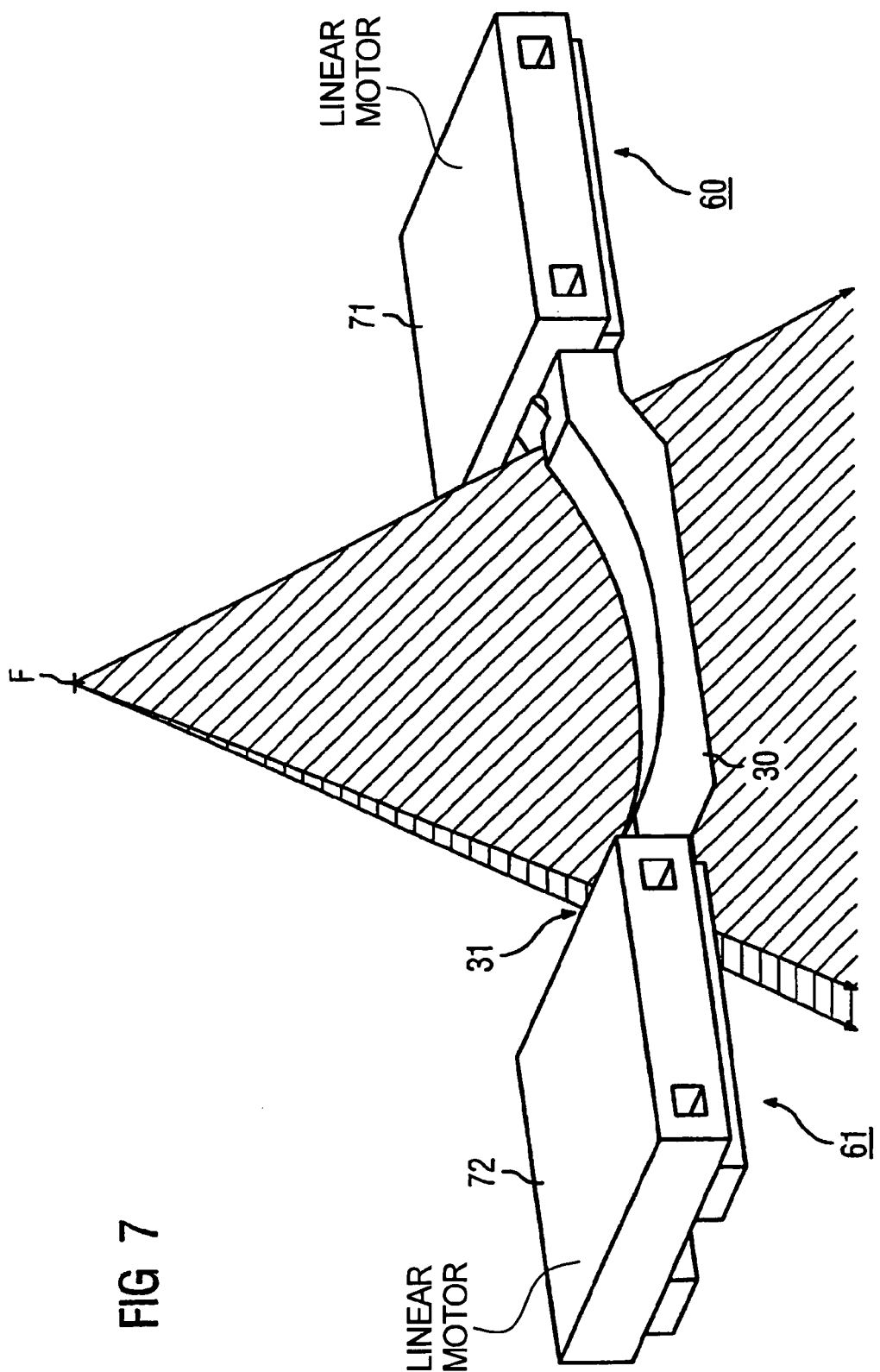
FIG. 7 is a perspective view of a third embodiment of the diaphragm of FIG. 3, operable in accordance with the inventive method.

A third exemplary embodiment of the gating device according to FIG. 3 is shown in detail in FIG. 7. This exemplary embodiment is essentially identical to the exemplary embodiment according to FIG. 5, but differs by the respective adjustment units 60, 61 for the absorber elements

30 and 31 a first linear motor 71 with a guide and a second linear motor 72, likewise with corresponding guide.

Instead of a linear guide, other linear adjustment possibilities can be used.

With the gating device 3, in connection with a focus-phi-z regulated control, it is possible to make appropriate adjustments to account for variation of the focus position or focus size in the x-ray radiator 2 in the diaphragm adjustment.

Although modifications and changes may be suggested by those skilled in the art, it is the invention of the inventors to embody within the patent warranted heron all changes and modifications as reasonably and properly come within the scope of their contribution to the art.

The invention claim is:

1. A method for operating a computed tomography apparatus having an x-ray radiator, which emits an x-ray beam from a focus, a radiation detector at which said x-ray beam is incident on an active detection field of said radiation detector and a diaphragm disposed proximate said radiation detector in said x-ray beam, said diaphragm having oppositely disposed absorber elements linearly movable in said diaphragm toward and away from each other, each of said absorber elements being curved in said x-ray beam relative to said focus, and a movable support adapted to receive an examination subject thereon, said method comprising the steps of:

acquiring computed tomography data from the examination subject in a spiral scan of said subject by rotating said x-ray source and said radiation detector around said subject and around a system axis while irradiating said examination subject with said x-ray beam, and while moving said support with the examination subject thereon through said x-ray beam in a direction substantially parallel to said system axis; and during at least one of a beginning of said spiral scan or an end of said spiral scan, reducing exposure of said examination subject to said x-ray beam by dynamically varying a spacing between said absorber elements by asymmetrically displacing said absorber elements independently of each other in said diaphragm with respect to a line connecting said focus and a center of said active detection field.

2. A method as claimed in claim 1 comprising, before said beginning of said spiral scan, placing one of said absorber elements in a completely closed position in said diaphragm relative to said line, and placing the other of said absorber elements in a completely open position in said diaphragm relative to said line.

3. A method as claimed in claim 2 comprising after said beginning of said scan, opening said absorber element in said closed position in synchronization with said movement of said patient support during said spiral scan.

4. A method as claimed in claim 2 comprising, before an end of said spiral scan, closing said absorber element in said open position in synchronization with said movement of said support.

5. A method as claimed in claim 1 comprising displacing a first of said absorber elements in said diaphragm with a first drive connected to said first of said absorber elements, and displacing a second of said absorber elements in said diaphragm with a second drive, operated independently of said first drive, connected to said second of said absorber elements.

6. A method as claimed in claim 5 comprising mounting the respective absorber elements in said diaphragm for linear movement thereof by said first and second drives.

7. A method as claimed in claim 6 comprising moving said first of said absorber elements in said diaphragm along a first linear guide in said diaphragm and moving said second of said absorber elements along a second linear guide in said diaphragm.

8. A method as claimed in claim 6 comprising employing a first linear motor as said first drive and employing a second linear motor as said second drive.

9. A method as claimed in claim 1 comprising curving each of said absorber elements in a plane perpendicular to said system axis.

10. A method as claimed in claim 1 comprising curving each of said absorber elements along an arc of a circle having a center coinciding with said focus of said x-ray radiator.

11. A method as claimed in claim 1 comprising offsetting said absorber elements with respect to each other along said line by curving said absorber elements with respectively different curvature radii.

12. A method as claimed in claim 11 comprising differing said curvature radii from each other in amount in a range between 0.5% and 10% of an offset spacing between said absorber elements along said line.

* * * * *